United States Patent [19]

Anderson

[11] 4,360,323
[45] Nov. 23, 1982

[54] PROPORTIONING PUMPING SYSTEM FOR DIALYSIS MACHINES

[75] Inventor: Robert L. Anderson, Boulder, Colo.

[73] Assignee: Halbert Fischel, Los Angeles, Calif.

[21] Appl. No.: 743,224

[22] Filed: Nov. 19, 1976

[51] Int. Cl.³ .................. F04D 17/00; F04D 23/06
[52] U.S. Cl. .................. 417/349; 417/429; 417/518; 417/539; 91/40; 137/99
[58] Field of Search .............. 417/398, 399, 401, 318, 417/518, 539, 426, 429, 63, 349; 137/99; 91/40, 287, 330; 324/30 B

[56] References Cited

U.S. PATENT DOCUMENTS

| | | | |
|---|---|---|---|
| 2,093,344 | 9/1937 | Wandel | 417/63 |
| 2,792,156 | 5/1957 | Camp | 92/13.7 |
| 2,819,726 | 1/1958 | Rendel | 324/30 B |
| 3,506,025 | 4/1970 | Benjet | 137/99 |
| 3,556,679 | 1/1971 | Middlebusher et al. | 417/63 |
| 3,598,727 | 8/1971 | Willock | 137/99 |
| 3,737,073 | 6/1973 | Lupert | 417/401 |
| 3,815,621 | 6/1974 | Robinson | 417/399 |
| 3,888,552 | 6/1975 | Fontaine | 417/401 |

FOREIGN PATENT DOCUMENTS

| | | | |
|---|---|---|---|
| 2262768 | 8/1973 | Fed. Rep. of Germany | 137/99 |
| 412997 | 7/1934 | United Kingdom | 417/63 |

*Primary Examiner*—Leonard E. Smith
*Attorney, Agent, or Firm*—Fraser and Bogucki

[57] ABSTRACT

A compact and highly reliable proportioning pumping system for supplying a precise and controllable mixture of concentrate and water in a kidney dialysis machine comprises a central body and a pair of oppositely mounted pivotable linkages coupled to the body. A first pivotable linkage is coupled by connecting rods to a water metering piston and a concentrate metering piston respectively, a variable stroke ratio being provided by a signal actuated drive coupled to the linkage mechanism and controlling the relative position of the end of one of the connecting rods. The change of position is advantageously effected so as to maintain a precise proportionality between the flows delivered by each of the pistons throughout their variable stroke lengths. The range of proportioning adjustments can be mechanically limited and alarm conditions can readily be detected. Precise delivery of surge-free flows of liquid for subsequent mixing is enhanced by controlling flow through each piston with a fast-acting metering valve system. A bistable switching valve responsive to the limit positions of the first linkage mechanism controls an actuator piston to operate a second pivotable linkage mechanism to which the metering valves are coupled. The second linkage switches rapidly between two alternate valve positions, so that there is a minimum dead zone and both water and concentrate flows are precisely controlled.

13 Claims, 9 Drawing Figures

PROPORTIONING PUMPING SYSTEM FOR DIALYSIS MACHINES

BACKGROUND OF THE INVENTION

In a dialysis machines and other life support systems a precisely proportioned supply of two liquids is often required to be provided with particular reliability and stability. In a dialyzer for an artificial kidney system, for example, a supply of water is fed in a selected nominal ratio, such as 34:1, relative to a concentrate with which it is mixed. While it is feasible to detect the proportion of the concentrate in the mixture, as by using a conductivity cell, the problems involved in safely and accurately pumping and controlling a variable water-concentrate have not heretofore been satisfactorily overcome.

In most prior art systems the approach has generally been to use either a fixed proportion pumping system or to employ a fully servo controlled system. In the fixed proportion displacement pumping system, the proportion of delivery of each liquid is initially precisely set, but this is not satisfactory for long term operation inasmuch as wear and changes in concentrate characteristics or other factors can cause the pumping system to go out of adjustment. In addition, it is not sufficient merely to deliver a precise ratio of the two liquids on a long term basis, inasmuch as short term factors are also very important. Because piston speeds with common types of proportional drives vary sinusoidally, unequal flows can occur at different times in the stroke, and this cannot satisfactorily be compensated by faster speed operation, which tends to introduce substantial wear and which also introduces surges in the flow. The use of a large mixing chamber is not desirable, because this substantially increases the problem involved in sterilizing the unit.

The servo techniques that have been applied have typically assumed complete authority over the constituent flows, but at the expense of substantially greater risk. The failure of any detector, circuit or component can result in malfunctioning of the equipment and severe harm to the patient. A complete failure of key components is not required, inasmuch as simple malfunctioning of particular components can result in a catastrophic situation from the standpoint of the patient. It is not desirable to rely upon energy sources which are subject to failure, or to utilize pumping systems which do not insure positive displacement of fluid.

SUMMARY OF THE INVENTION

Systems in accordance with the invention provide highly reliable positive displacement of two liquids in precisely defined but adjustable ratios by providing variable stroke ratios in controlling metering pistons with a pivotable linkage. A fine tuning of the mixing ratio, responsive to detection of the properties of the mixture itself, may be made by adjustment of the stroke length of at least one of the pistons. Concurrently, flows metered by the pistons in bidirectional operation are controlled by a bistable metering valve system which shifts rapidly between opposite limits of movement in response to the movement of the linkage mechanism.

In a particular example of a proportioning pump system for controlling the flow of water and concentrate in a kidney dialysis machine, a pair of pivotable linkage mechanisms are coupled to different parts of a body defining piston and valve cylinders, and including an internal conduit system. A first pivotable linkage is coupled to control the length of stroke of a water metering piston and a concentrate metering piston respectively, the stroke ratio being made adjustable by a controlled position follower in the linkage mechanism and coupled to one end of a connecting rod for one of the metering pistons. Power for driving the two pistons is derived from the pressurized water itself. Detection of a variation in the mixture is used to provide a servo signal to a drive motor mounted on the linkage mechanism and controlling a variable position device that governs the position of the follower. The relative change of position is precisely controlled to provide optimum matching of the flow rates of the two pistons throughout the range of stroke ratio adjustments. Extremes of movement of the follower device are utilized to define limiting conditions within which the pumping ratio is affirmatively maintained. Additionally, switches disposed adjacent the follower mechanism may also be utilized to indicate the existence of limit conditions for the operator.

In accordance with other aspects of the invention, the precision and surge-free operation of the proportioning pumping system are enhanced by a bistable metering valve system which controls liquid flow through the two bidirectional pistons. Switching valve means coupled to be controlled by the first linkage means controls flow of pressurized tap water to either side of an actuator piston, to provide power for pivotting a second linkage mechanism. Substantial play in the switching valve coupling is used, so that the valve is shuttled rapidly from one limit position to another, as the first linkage mechanism approaches each end of its reciprocating travel. Responsively, the actuator piston also rapidly shifts from one limit to another, and a rod connected from the actuator piston to the second pivotable linkage mechanism correspondingly controls the position of one or more metering slide valves which control flow through one side or the other of the metering pistons. Thus there is a minimum dead zone while the pistons are reversing directions and the flows are precisely metered.

BRIEF DESCRIPTION OF THE DRAWINGS

A better understanding of the invention may be had by reference to the following description, taken in conjunction with the accompanying drawings, in which.

DETAILED DESCRIPTION

Figure 1:
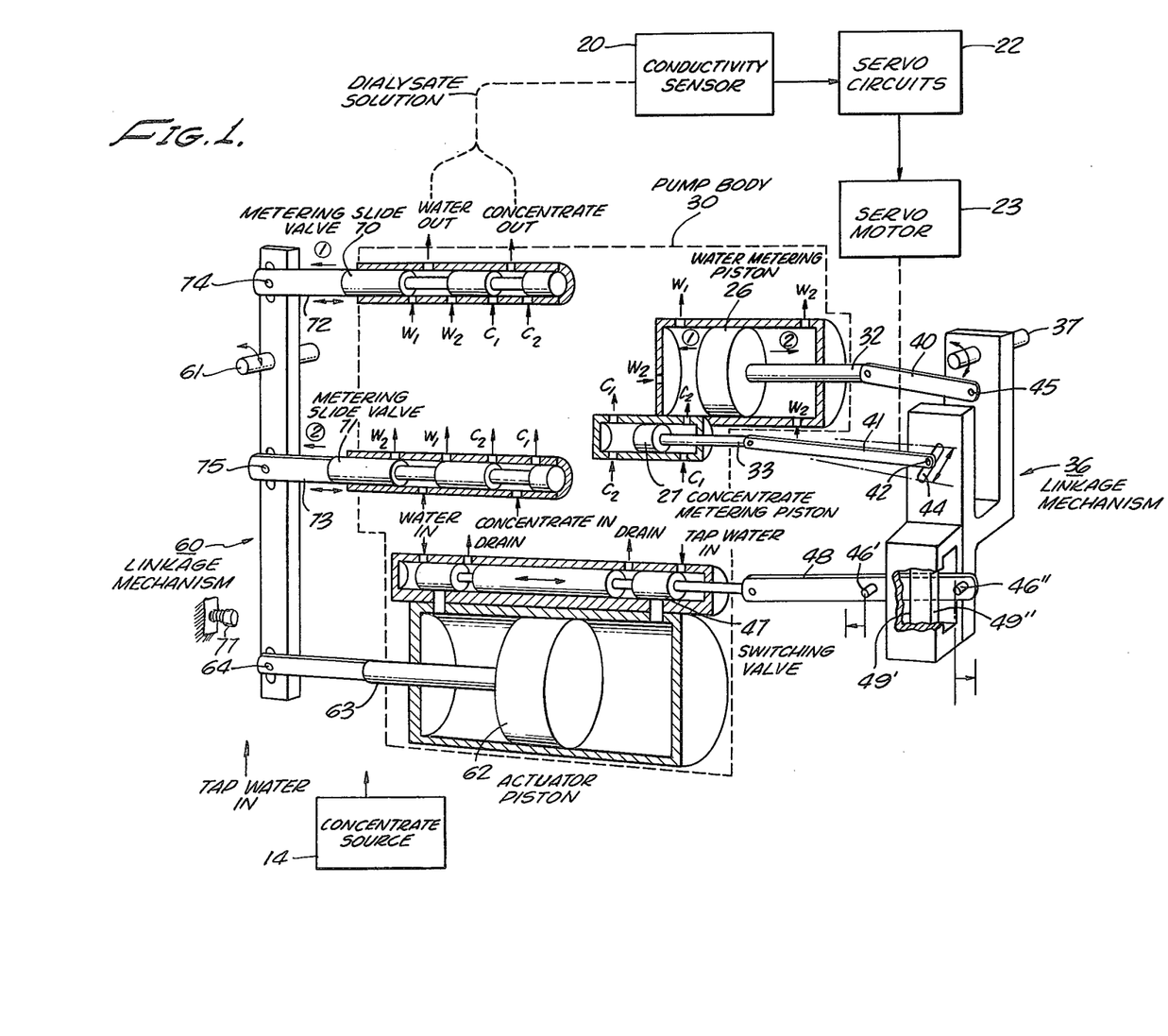
FIG. 1 is a simplified, broken away perspective and block diagram representation of the principal elements of a system in accordance with the invention, showing the proportioning pump system and elements of a dialysis machine associated therewith.

FIG. 1 depicts in generalized form only those principal elements of any one of a number of known types of artificial kidney machines with which devices in accordance with the present invention may be utilized. A proportioning pump system 10 receives tap water from an external source (not shown), which water is typically degassified either before or after use in the proportioning pump system 10. Concentrate from a concentrate source 14 is also supplied to the proportioning pump system 10, which delivers a dialysate of mixed water and concentrate to a common conduit or small mixing chamber. This dialysate solution is passed from the common conduit through a conductivity sensor 20 within the system. The conductivity sensor 20, which may be the improved type of device described in copending application Ser. No. 599,691, filed July 28, 1975, now U.S. Pat. No. 4,035,719, issued July 12, 1977 generates an electrical signal representative of the proportion of concentrate in the solution, and applies this signal to servo circuits 22, which provides an output signal to a servo motor 23 that controls a mixing ratio adjustment device (described in detail hereafter) in the proportioning pump system 10.

Inasmuch as the principal operative elements in the pump system 10 are shown only in generalized and schematic form in FIG. 1, reference will also be made to various other figures for a more detailed understanding of the specific arrangement. To provide the desired proportions of water and concentrate flow, a relatively large and bidirectionally operative water metering piston 26 mounted to reciprocate along a first axis and a concentrate metering piston 27 reciprocable along a parallel axis are mounted together in a pump body 30, which is depicted in FIG. 1 only by dotted lines. A piston rod 32 for the water metering piston 26 and a piston rod 33 for the concentrate metering piston 27 extend outwardly from one side of the pump body 30. The pistons 26, 27 are mounted somewhat side-by-side, within the body 30, in order to achieve compactness. A first pivotable linkage mechanism 36 is mounted on the side of the pump body 30 adjacent the piston rods 32, 33, being coupled to pivot about a fixed pivot pin 37. The linkage mechanism 36 is depicted in simplified form in FIG. 1 as an integral assembly of linear sections, and reference should be made to the other figures for details as to a specific example. Connecting rods 40, 41 couple the respective piston rods 32, 33 to different spaced-apart regions on the first linkage mechanism 36. The free end of the connecting rod 41 for the concentrate metering piston 27 is coupled to the linkage mechanism 36 by a variable position device controlled by the servo motor 23. In FIG. 1, a follower pin 42 attached to the rod 41 near its free end moves within an angled slot 44 in the linkage mechanism 36, while the other connecting rod 40 is coupled to a pivotable pin 45 in the linkage mechanism. In FIGS. 2–8, a lead screw variable position device is depicted and described for the specific purpose of controlling the follower 42.

The pump body 30 also includes a cylinder receiving a linear switching valve 47 which is pivotally coupled to one end of a floating rod 48 extending within an aperture in the linkage mechanism 36. The floating rod 48 includes a pair of spaced-apart limit pins 46', 46" extending transversely from different points along its length. The floating rod 48 is free to shift within the apertures in the linkage mechanism 36, except when that mechanism approaches its limit positions. Then either limit pin 46', 46" engages a facing internal shoulder 49', 49" which then carries the floating rod 48 to the final increment of movement. Consequently, the switching valve 47 shuttles periodically between two switching positions at successive spaced-apart times coincident with incipient changes of direction of the linkage mechanism 36. Thus when the linkage mechanism 36 pivots about its fixed axis at the pivot pin 37, the pistons 26, 27 reciprocate concurrently with different stroke lengths depending upon their spacing from the pivot axis, and upon the location of the free end of the connecting rod 41. The stroke length of the concentrate metering piston 27 is variable in this example, although it will be appreciated that either or both the piston strokes may be varied if desired for some reason.

Figure 2:
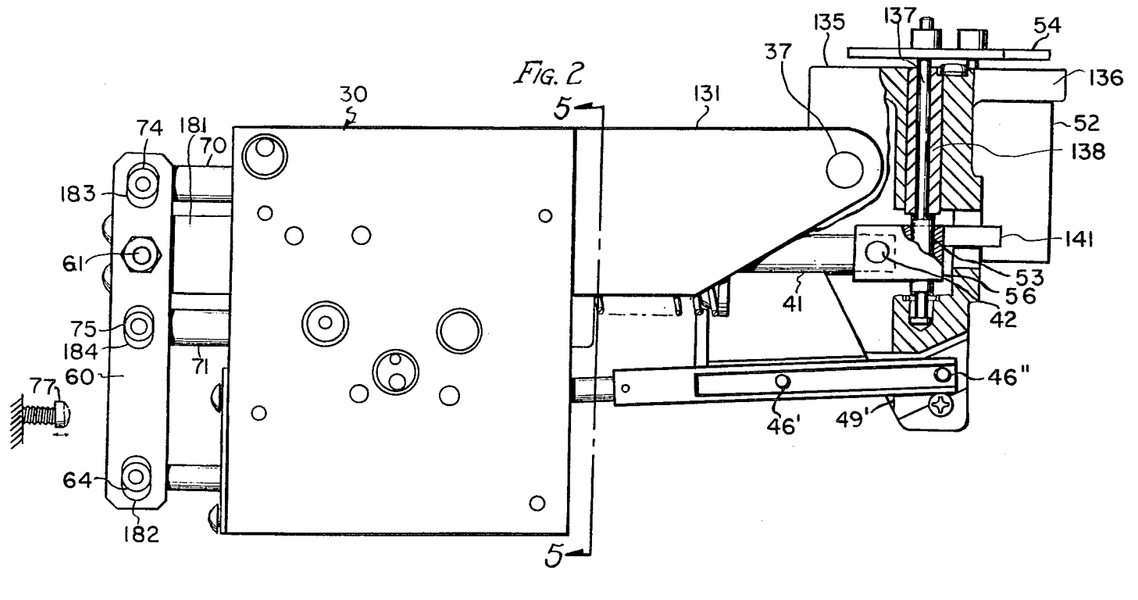
FIG. 2 is a side view, partially broken away, of a proportioning pump system in accordance with the invention.
Figure 3:
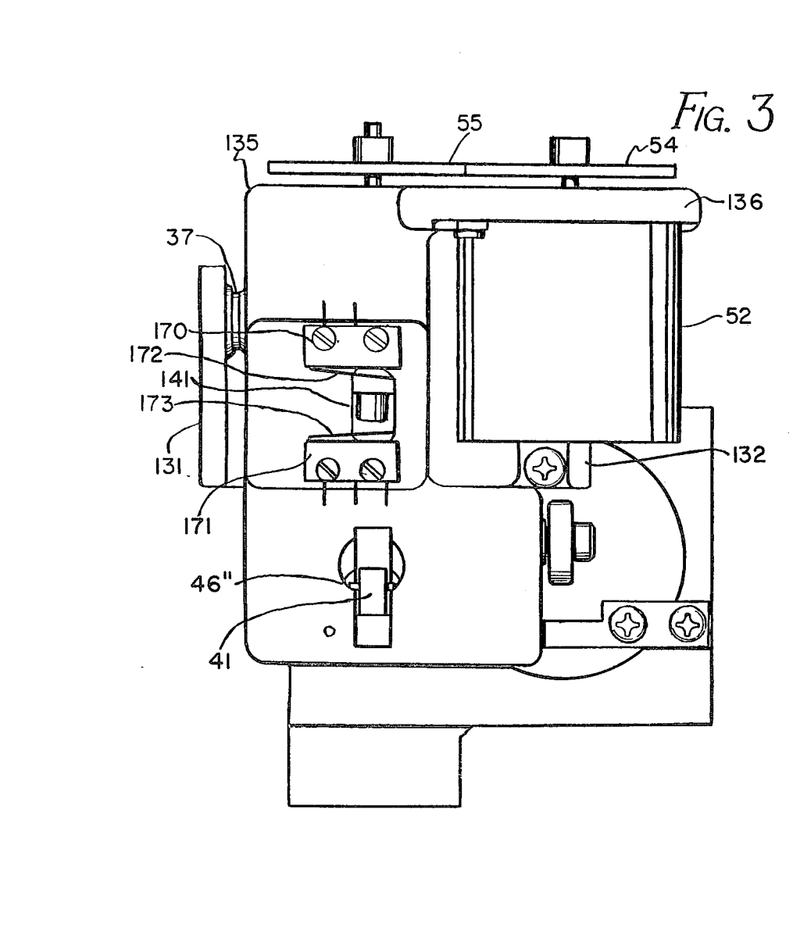
FIG. 3 is one end view of the arrangement of FIG. 2.
Figure 9:
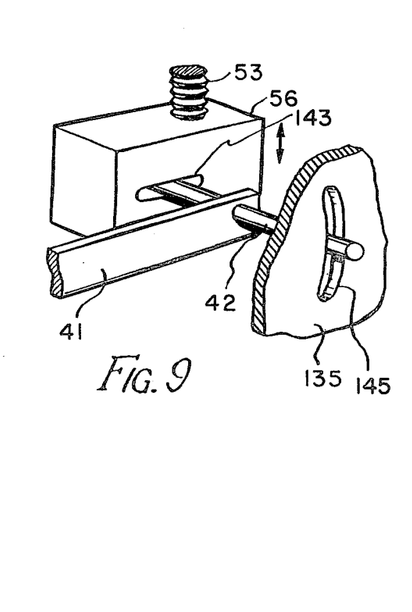
FIG. 9 is a fragmentary perspective view of a position adjustment mechanism that may be employed in the system of FIGS. 2–8.

Reference should here be made to FIGS. 2 and 3 to clarify the specific construction of the variable position device that is used in the detailed example. To control the stroke length of the water metering piston 26 between predetermined limits, the servo motor 23 is mounted on the linkage mechanism 36 to drive a lead screw 53 through a pair of drive gears 54, 55. The lead screw 53 engages and changes the position of a mounting bearing 56 to which the connecting rod 41 is coupled by the follower pin 42. The angle of the lead screw 53 axis relative to the axis defined by a line along the axial centers of the pivot pin 37 and the pivot pin 45 for the rod 40 corresponds to the angle of the slot 44 in FIG. 1 with respect to the like reference axis. A more precise structure for controlling the stroke ratio is described below in conjunction with FIGS. 2 and 9.

At the opposite end of the pump system 10, returning now to FIG. 1, a second pivotable linkage mechanism 60 is mounted to pivot about a fixed pivot pin 61 coupled in fixed relation to the body 30. An actuator piston 62 disposed within a cylinder in the pump body is coupled by a connecting rod 63 to a pivot bearing 64 adjacent a lower end of the second linkage mechanism 60. A pair of metering slide valves 70, 71 are each coupled through a different connecting rod 72, 73 respectively to a different pivot bearing 74 or 75 respectively on the second linkage mechanism 60. The position of the second linkage mechanism 60 is controlled by the actuator piston 62, which quickly moves the metering slide valves 70, 71 from one limit position to another in synchronism with changes in movement of the first pivotable linkage mechanism 36. The metering valves 70, 71 then control the direction of feed of water and concentrate through the metering piston devices 26, 27. An adjustable stop 77 mounted on a fixed base (which may be part of the body 30) is positioned to limit the pivotting of the second linkage mechanism 60 in one direction (here viewed as the clockwise direction).

Figure 7:
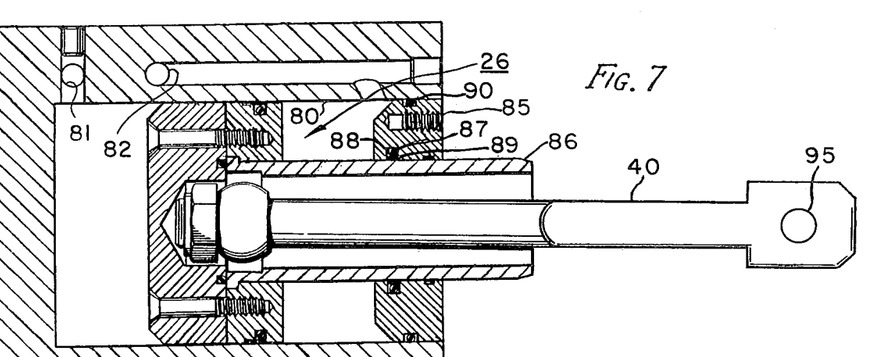
FIG. 7 is a side sectional view of a water metering piston employed in the arrangement of FIGS. 1 and 2 showing further details thereof.

The proportioned pumping action of the system is controlled by the water metering piston 26 and the concentrate piston 27, and reference should be made to FIG. 7 for a more detailed view of the specific arrangement of the water metering piston 26. In FIG. 7, the piston 26 reciprocates within a cylinder 80, pumping bidirectionally through an orifice 81 at its head or forward side and through an orifice 82 at its rear or reverse side. The piston 26 is shown in its central position, and includes a cylindrical piston rod 40 extending through an end sleeve 86 seated in a gland 85 which provides a sliding seal for the piston rod. To provide an effective zero leakage seal, at the inner periphery of the end sleeve 86, an O-ring 87 disposed within a circumferential channel 88 in the gland 85 bears against a "Glyd" ring 89 which registers with the surface of the sleeve 86. This combination provides an effective zero leakage seal, with the "Glyd" ring providing a smooth contact, low wearing surface at its relatively undistortable and the O-ring providing resilience. This combination is used for zero leakage seals extensively throughout the mechanism, but for brevity only this particular usage is described, and it would be understood that the same description is applicable to the remaining instances. A number of O-rings are also used within the system for minimizing leakage, as with the outer O-ring 90 disposed between the retaining hub 89 for the end sleeve 86 and the cylinder wall 80. The water metering piston 26 is coupled directly to the first pivotable linkage mechanism 36 by an end pivot bearing 95 which is coupled to the connecting rod 40 (not shown in FIG. 7).

Figure 6:
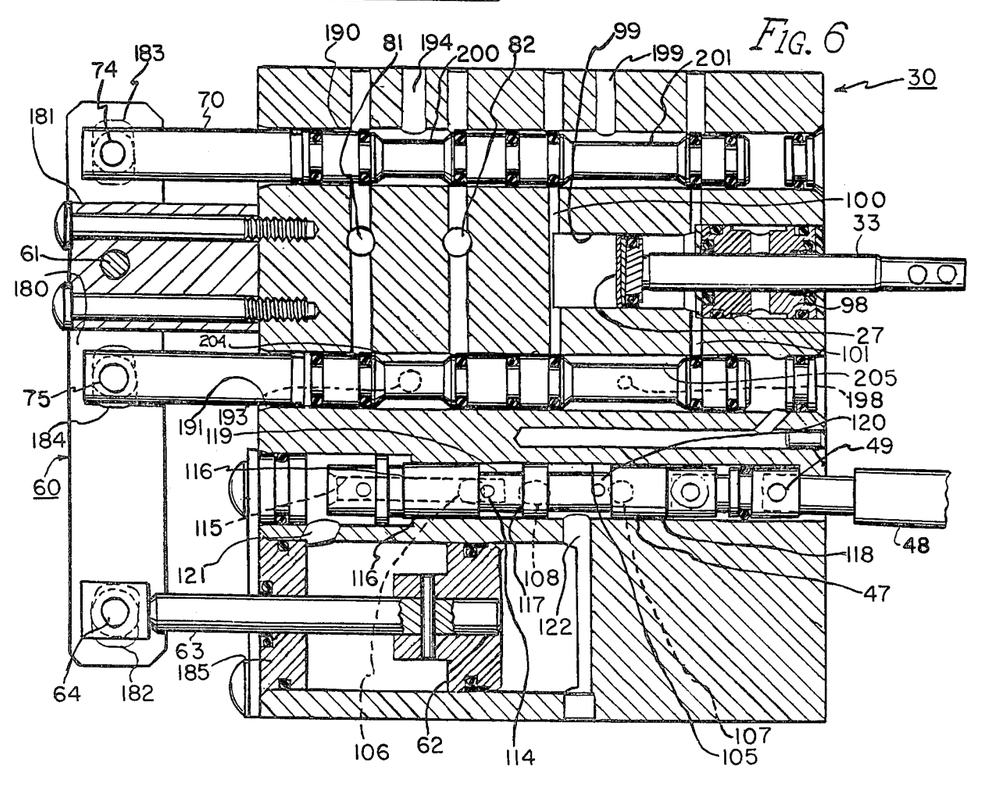
FIG. 6 is a side sectional view of a part of the arrangement of FIG. 4, taken along the lines 6—6 in FIG. 4.

At thee concentrate metering piston 27, best seen in FIG. 6, the piston rod 33 extends outwardly through an end gland 98. In a widened portion of the cylinder wall 99 a conduit 100 traverses the forward end of the interior volume of the cylinder, and a separate conduit 101 traverses the rearward end of the interior volume. The concentrate metering piston 27 is shown in the intermediate position, and reciprocates along an axis substantially parallel to the axis of the water metering piston 26.

Also coupled to the first pivotable linkage mechanism 36, as seen in FIGS. 2, 3 and 6, is the linear switching valve 47 which is reciprocated via the connecting rod 48 and pivot pin 49 at the first end of the pump body 30. The switching valve 47 reciprocates within a cylinder wall 105 which includes two spaced-apart drain outlets 106, 107 and an intermediate tap water inlet 108. The switching valve 47 is configured with a terminal bore 115 which extends to a predetermined depth from the free end of the valve 47 and a set of three spaced-apart rings 116, 117, 118 separated by smaller diameter shafts 119 and 120, and all located in the vicinity of the outlets and inlets 106–108. Linear movement of the switching valve 47 along its axis parallel to the first axis provides communication between the tap water inlet 108 and either of two conduits 121, 122 leading into the adjacent actuator piston cylinder, while alternately coupling the side that is not receiving inlet water to the appropriate drain outlet 106 or 107.

The first pivotable linkage mechanism 36, best seen in FIGS. 2 and 3, is mounted on a pair of brackets 131, 133 coupled to the pump body 30 at the first end thereof. A cross shaft 37 supports a linkage housing 135 shown in substantially vertical disposition in these figures, although the housing actually oscillates about the cross shaft 133 during operation. The motor 52 is mounted on a bracket 136 extending from a side of the housing 135, so that the motor 52 shaft is upwardly directed, and supports an associated drive gear 54 which rotates the adjacent gear 55 mounted on a shaft 137 (FIG. 2) within a bushing 138 in the housing 135. The lead screw 53 coupled to the shaft 137 registers within a lead nut 56, best seen in FIG. 2, within the housing 135, the lead nut 56 having an extending tab 141 at its free end, and a lateral aperture for receiving a pivot pin 42 coupled to the extending end of the connecting rod 41 for the concentrate metering piston 27. The longitudinal axis of the lead screw 53 is set, in this example, at an angle of approximately 24° to the effective axis of the linkage, which is defined as the axis defined by a line between the centers of the pins coupled to the connecting rods for the water metering piston 26 and the concentrate metering piston 27.

As depicted in FIGS. 2 to 8, the stroke ratio, and therefore the concentration is adjusted by linearly varying the position of the lead nut 56 along its axis. This type of control is adequate for many proportioning situations, including a number of dialysis applications. Thus where the dialysate is fed into and taken from a bath, instantaneous variations are averaged by mixing in the bath, and there is sufficient accuracy in the proportions for most uses. However, where control of the concentrate must be more precise and only a small mixing volume can be used, the position of the pin 42 relative to the linkage is varied in two dimensions. As shown in expanded form for clarity in FIG. 9, the lead nut 56 then includes a slot 143 normal to its axis, for receiving the pin 42 and controlling its position relative to said axis. The linkage body 135 also contains a slightly curved slot 145, which is generally concave towards the metering piston 27. Thus, a change in lead nut 56 position along its axis causes the pin 42 to be constrained to a specific position along horizontal and vertical references.

The curvature of the slot or locus of displacement of the pivot point where the connecting rod to the concentrate piston pivots on the link is defined as follows:

The function:

$$f_1(a_1, \theta) = (b_1^2 - [a_1 \cos\theta - c_1]^2)^{\frac{1}{2}} + a_1 \sin\theta$$

represents the perpendicular distance of the concentrate piston pivot from an axis which is orthogonal to the piston axis i.e., center line through the pistons, and passes through the link pivot point 37. This distance is expressed as a function of $\theta$, the angle made by the link with respect to the axis orthogonal to the piston axes aforementioned, as the link oscillates with the reciprocal motion of the pistons. $a_1$ is the distance between the concentrate piston connecting rod pivot point on the link and the link pivot point; $b_1$ is the length of the connecting rod as measured between its pivot points at either end; and $c_1$ is the fixed normal distance between the link pivot 37 and the concentrate piston axis. A subscript 2 refers to similar parameters as measured with respect to the water piston.

The piston displacements are then given by:

$$D_1 = f_1(a_1, \theta) - f_1(a_1, 0)$$

$$D_2 = f_2(\theta) - f_2(0)$$

The object is to define a geometry for which the relative displacements of concentrate and water pistons are strictly proportional throughout the stroke. If this is not the case the mixing ratio oscillates with an objectionable magnitude about a mean value with each cycle of the pistons.

If similarity between geometrical parameters is imposed, i.e., $$\frac{a_1}{a_2} = \frac{b_1}{b_2} = \frac{c_1}{c_2}.$$

then:

$$\frac{b_1}{a_1} = \frac{b_2}{a_2} \text{ and } \frac{c_1}{a_1} = \frac{c_2}{a_2}$$

whereupon:

$$\frac{D_1}{D_2} = \frac{a_1}{a_2}$$

which is a constant independent of $\theta$, a result which signifies uniform proportionality of piston displacements throughout the stroke.

However, in order to servo the mixing ratio it is necessary to alter the proportionality and this cannot be done with respect to all parameters as would otherwise be required to preserve strict geometrical similarity. A compromise would be to displace one parameter in a manner which produces the least variability of mixing ratio as a function of stroke position. In the example shown the parameter $a_1$ is displaced by $\delta a_1$. If this were the only change a piston displacement ratio which is asymmetric with respect to the center position, i.e. $\theta = 0$ as shown in figure B results. In order to mitigate the variation of piston displacement ratio a phase angle $\delta\theta_1$ is introduced along the pivot displacement $\delta a_1$. Then:

$$D_1 = f_1(a_1 + \delta a_1, \theta + \delta\theta_1) - f_1(a_1 = \delta a_1, \delta\theta_1)$$

$D_2$ is unaltered.

The object is to find a function, $F(\delta\theta_1, \delta a_1) = 0$ such that the R.M.S. deviation of mixing ratio $D_1/D_2$ with respect to a mean value is a minimum. The mean value is:

$$\left(\frac{D_1}{D_2}\right) = \frac{1}{2_1\theta_1} \int_{-1\theta_1}^{+1\theta_1} \left(\frac{D_1}{D_2}\right) d\theta$$

and $$\frac{\partial}{\partial(\delta\theta_1)} \int_{-1\theta_1}^{+1\theta_1} \left[\frac{D_1}{D_2} - \left(\frac{D_1}{D_2}\right)\right]^2 d\theta = 0$$

The above equations define an exact solution to what is, at best, a compromise with respect to the ideal of exact geometrical similarity. This compromise is affected only to a limited extent by imposing upon the function $F(\delta\theta_1, \delta a_1) = 0$ a linear relationship such that the concentrate connecting rod pivot on the link is shifted along a straight line (as in FIGS. 2-8) which is skewed with respect to the link axis defined by a line through the link pivot point and the water piston connecting rod pivot on the link. This line includes the unshifted position of the concentrate connecting rod pivot point on the link.

In the present case in which the nominal mixing ratio is one part concentrate to 34 parts water, the desired servo limits are ±5% from nominal. The best curve fit produces a mixing ratio oscillation of less than ±½% at the extreme servo positions. The best curve fit calls for an inclination of the aperture 143 of 14° with respect to the link axis.

Other means are possible for causing the shifting of the concentrate piston connecting rod pivot point on the link in the manner described above without the use of a slotted aperture in the link.

For computational purposes to simplify integration it is generally sufficient to approximate $(a_i \cos\theta - c_i)$ by $a_i(\cos\theta - 1) = 2a_i \sin^2\theta/2$ since $a_i$ and $c_i$ are nearly equal. Further, one can write $\theta \approx \sin\theta$ and still preserve the skewed nature of the displacement ratio variation to an excellent approximation. The function $f_i$ then becomes:

$$f_i(a_i, \theta) = \left(b_i^2 - \frac{a_1^2}{4}\theta^4\right)^{\frac{1}{2}} + a_i\theta$$

The solution $F(\delta\theta_1, \delta a_i) = 0$ is given by:

$$(a_1 + \delta a_1)[\cos\delta\theta_1 + \sin\delta\theta_1 \cot d] - a_1 = 0$$

where d is the 24° angle. This defines a linear deflection of the pivot pin 37 rather than a curved one. To obtain a curved aperture solution one retains higher order terms in the approximation of $\sin\theta$ for the relatively small degree of improvement that can then be achieved.

Figure 8:
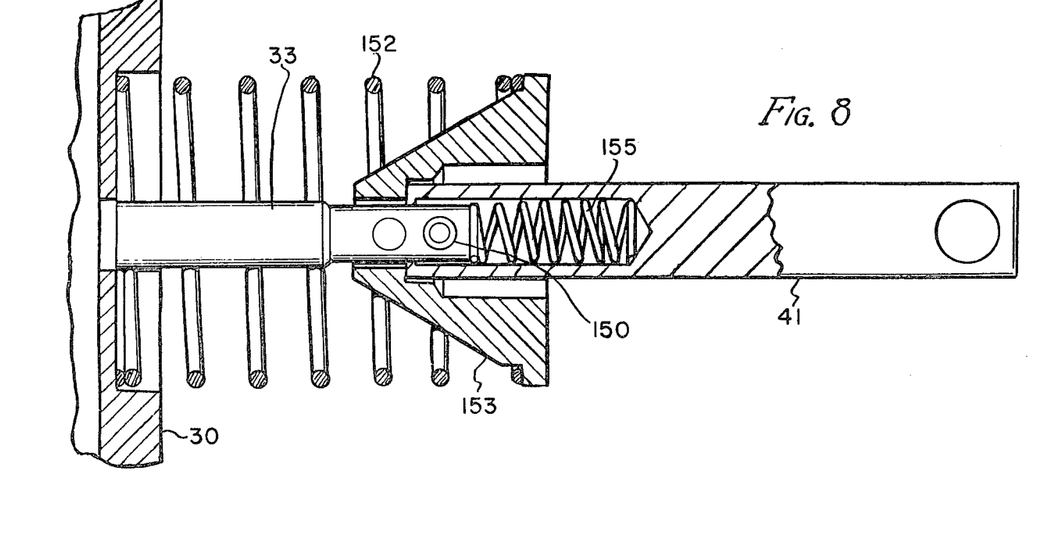
FIG. 8 is a side sectional view of a spring loaded mechamism employed in the arrangement of FIGS. 1 and 2.

At the concentrate metering piston 26, as seen in FIG. 8, the piston rod 33 and connecting rod 41 are coupled by a pivot pin 150. Additionally, however, force loadings in the system are balanced by a concentric exterior spring 152 between the wall of the pump body 30 and a spaced-apart guide 153, to urge the concentrate metering piston mechanism in the reverse direction. Also, the connecting rod 41 includes a terminal bore encompassing the adjacent end of the piston rod 33, and an interior helical spring 155 urges the connecting rod 41 in the reverse direction relative to the rod 33. This spring loaded mechanism counteracts play in the components of the system.

Above and below the extending tab 141 (FIG. 3) on the lead nut 56 are disposed a pair of small switches 170, 171 (e.g. "Microswitches") whose extending contacts 172, 173 respectively are engageable by the tab 141 in the upper and lower limiting positions of movement.

Figure 4:
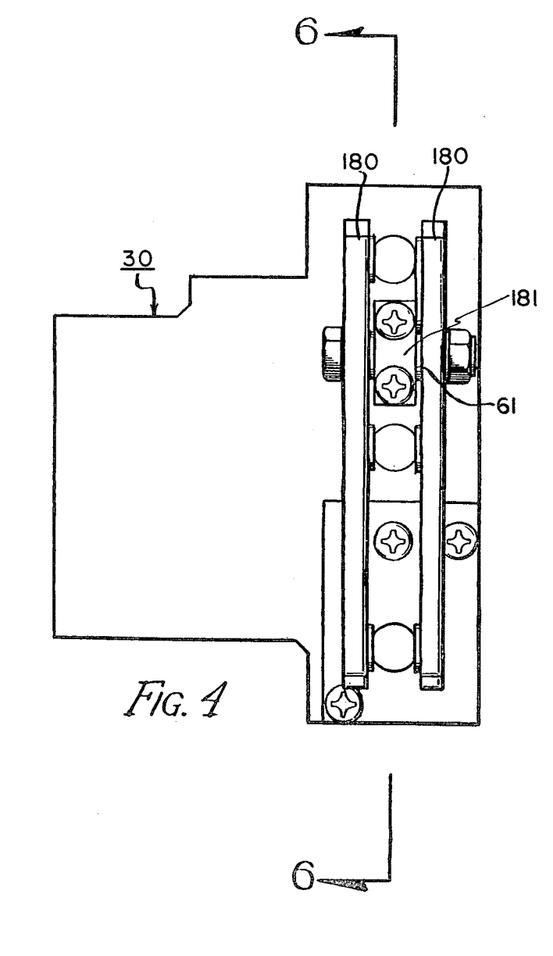
FIG. 4 is another end view of the arrangement of FIG. 2.
Figure 5:
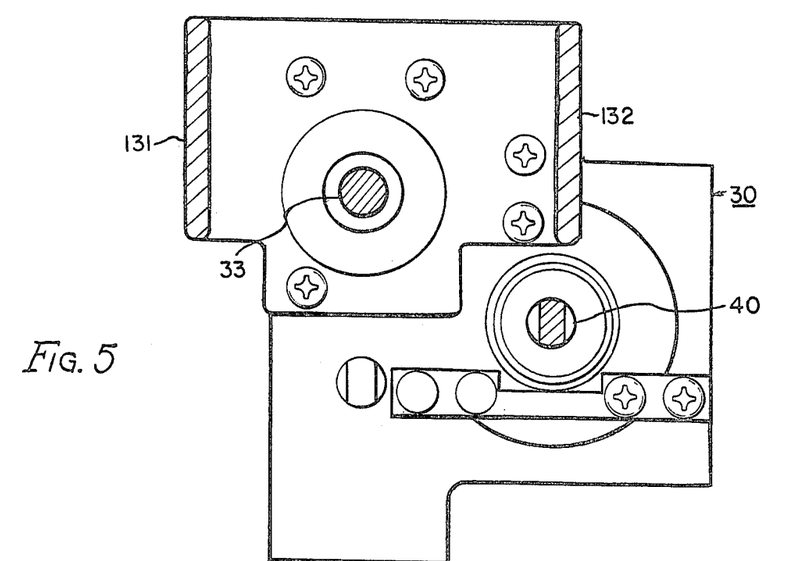
FIG. 5 is an end view corresponding to FIG. 3, but, taken along the lines 5—5 in FIG. 2.

The second pivotable linkage mechanism 60, best seen in FIGS. 2, 4 and 6, is disposed at the opposite end of the valve body 30 from the first pivotable linkage mechanism 36, and is mounted on a double elongated pivot body 180 so as to turn around the included pivot pin 61 which is seated within a bracket 181. The pivot pins 64, 74, 75 extending transversely relative to the longitudinal axes of the actuator piston rod 63, the upper slide valve 70 and the lower slide valve 71 respectively rest in elongated slots 182, 183 and 184 respectively in the second pivotable linkage mechanism 60, to provide allowance for change of position of the linkage mechanism relative to the axially moving valve and rod members, in conventional fashion.

The metering slide valves 70, 71 (referring now to FIG. 6) each register within separate cylindrical wall apertures 190, 191 disposed substantially horizontally within the valve body 30. Although a single metering slide valve could be employed, the usage of two slide valves 70, 71 for inlet and outlet control permits substantially vertical flow of concentrate and water through the system, permitting included bubbles to rise by gravity and preventing the formation of substantial air masses within the system. The inlet for water comprises an aperture 193 in the lower slide valve cylinder wall 191, from which the water may pass to either the forward or reverse orifice 81, 82, under control of the lower slide valve 71, and then as controlled by the upper slide valve 70 to an outlet orifice 194. Similarly the concentrate inlet 198 comprises an aperture in the cylinder wall 191 communicating with the conduits 100, 101 which direct the concentrate upwardly to the concentrate cylinder 99 and piston 27. Then, as controlled by the upper slide valve 70, the concentrate passes at an outlet 199.

Each of the metering slide valves 70, 71 includes a number of the zero leakage seals, to provide assurance against interchange or loss of fluids. The slide valves 70, 71 are symmetrically disposed about the pivot pin 61, so that they may move with equal strokes although in opposite directions. However, the adjustable stop 77 of FIGS. 1 and 2 may be used to limit movement in one direction so as to equalize flows. The upper metering slide valve 70 includes a pair of neck valve sections 200, 201, of smaller diameter than the remainder of the valve, and of a length shorter than the center-to-center spacing between the adjacent conduit pairs 81, 82 or 100, 101 respectively. Similarly, the lower metering slide valve 71 includes a pair of neck valve portions 204, 205; both valves 70, 71 are shown in the central position in FIG. 6.

To review the operation of the proportioning pump system, the centrally disposed position of FIGS. 1, 2 and 6 will be assumed for the various pistons and valve members at the outset, and the directions "left" and "right" will be taken as viewed in the side views of FIGS. 1 and 6. Assume also a given position of the lead nut 56 (FIG. 2) is determined by the servo circuits 22. Assume also that the first pivotable linkage mechanism 36 is moving in the forward direction (clockwise in FIGS. 1 and 6), so that the water metering piston 26 and the concentrate metering piston 27 are moving to the left. It is important to note that under these conditions the midpoint depiction that is shown for the slide valve 70, 71 would not apply, but that instead the valve 70 would be at its extreme leftward position and the valve 71 would be at its extreme rightward position. This is due to the operation of the switching valve 47 and the actuator piston 62, the operation of which should be first understood. As the water metering piston 26 and concentrate metering piston 27 move forward, the switching valve 47 is at its extreme rightward position, and does not move in the opposite direction until the first linkage mechanism 36 approaches a limit position. Then the pin 46' (FIGS. 1 and 2) on the rod 48 is engaged by the internal shoulder 49' so as to shift switching valve 47 leftward. The central ring 117 (FIG. 6) on the valve 47 is moved rapidly from the righthand side of the water inlet 108 to the lefthand side of that inlet, changing water flow to the actuator piston 62 chamber. The switching valve 47 serves as part of a bistable or toggle hydraulic mechanism which quickly shifts the metering slide valves 70, 71 to their opposite limit positions. Specifically, when the center ring 117 of the switching valve 47 is moved forward, with the center ring 117 to the left of the water inlet 108, water flow from the inlet 108 goes around the narrow shaft portion 120 of the switching valve 47, and into the chamber at the righthand side of the actuator piston 62. The force of the inlet water acts on the righthand surface of the piston 62, while the drain outlet 106 was also opened by leftward movement of the ring 116 to the lefthand volume of the piston 62. Drain water flows out of the lefthand volume, through the bore 115 and through the aperture 114 in the wall of the slide valve 47 into communication with the drain outlet 106. Thus by forcing water into the righthand volume to the actuator piston 62, while it is forced out of the lefthand volume, the actuator piston 62 quickly moves to its extreme clockwise limit. By virtue of the second linkage mechanism 60, the lower metering slide valve 71 was shuttled to its lefthand limit, and the upper metering slide valve 72 to its righthand limit. When the actuator piston 62 reaches its extreme forward (lefthand) position the linkage mechanism 60 and the devices coupled thereto hold position until substantial completion of the relatively slow reverse motion of the pistons 26, 27. Just prior to the completion of the counterclockwise movement of the linkage mechanism 36 about its axis, the reverse pin 46" on the connecting rod 48 is engaged by the internal shoulder 49" (as it moves toward the right). This contact shifts the rod 48 to the right, moving the center ring 117 to the right of the water inlet 108, with the ring 118 exposing the drain outlet 107 to the interior volume adjacent the actuator piston 62 via the conduit 122, and with the inlet water passing through the aperture 114 and the bore 115 into the lefthand portion of the actuator piston 62 volume through the conduit 121.

This bistable hydraulic function is effected without imposing any significant load on the slowly moving and precisely metering pistons 26, 27. Power for actuation of the first pivotable linkage mechanism 36 is derived from the pressure of the water on either face of the water metering piston 26. This is a large surface area piston and the pumping rates are low, so that only a relatively low pumping pressure is required. Power for shifting of the second pivotable linkage mechanism 60 is derived from tap water pressure at the actuator piston 62, which again is of substantial cross-sectional area relative to the remainder of the components.

The functioning of the bistable hydraulic toggle system therefore insures rapid shifting of the metering slide valves 70, 71 between two limit positions. Inasmuch as the two valves move in opposite senses it would be confusing to refer to forward and reverse directions as to these elements. Therefore, when the pistons 26, 27 are in their forward direction of movement, the slide valves 70, 71 will be referred to in a first position, and when the pistons are in the reverse direction of movement the slide valves 70, 71 will be referred to as in a second stable position. In the first stable position, the upper slide valve 70 is at its lefthand limit, with the neck valve portions 200, 201 communicating with the conduits 81 and 100 respectively. The lower slide metering slide valve 71, in its first position, has its neck valve portions 204, 205 in communication with the conduits 82 and 101 respectively. In the first position, therefore, water at the inlet 193 is passed through the conduit 82 (FIG. 6) into the reverse side volume adjacent the water metering piston 26, continuing to urge the piston 26 forward. At the same time, the forward face of the water metering piston 26 forces water out of the chamber through the conduit 81, and this water goes about the neck valve 200 within the cylinder 190 and out the water outlet 194.

Concurrently, at the concentrate side, concentrate at the inlet 198 passes through the conduit 101 with which the neck valve portion 205 is in communication, and into the reverse side volume adjacent the concentrate metering piston 27, forcing it forward. The flow outward from the conduit 101 is blocked by the upper slide valve 70, which is in its left position, but concurrently concentrate is being forced out of the conduit 100, around the neck valve portion 201 of the upper slide valve 70 and out the outlet 199. In symmetrical fashion, in the second position of operation water is directed from the inlet 193 through the conduit 81 into the water metering piston 26 on one side, and out from the opposite side of the conduit 82 past the neck valve portion 200 and out the outlet conduit 194, while concentrate from the inlet 198 is directed through the conduit 100 into the lefthand volume of the adjacent concentrate metering piston 27 and out the righthand side past the neck valve portion 201 of the upper metering valve 70 to the concentrate outlet 199.

The rapid shifting of the upper and lower metering slide valves 70, 71 occurs in a fraction of the time required for the pistons 26, 27 to turn around, so that the pumping and metering actions are smooth and continuous over the great majority of the stroke, and then flow briefly stops as direction is shifted. The adjustable stop 77 (FIGS. 1 and 2) is employed as a useful compensation feature. Because the water metering piston 26 which supplies power has a larger surface area on its left face than its right due to the presence of the piston rod 40 and sleeve 86, a force differential exists between the forward and reverse directions. The reverse (rightward in this example) movement of the piston 26 and the other elements linked to it is faster than the forward movement as a result. To compensate, the second linkage mechanism 60 is held short of its extreme clockwise limit by the adjustable stop 77, slightly restricting flow rates into and out of the chambers of the pistons 26, 27 as they move rightward and thus slowing down the reverse movement so that the bidirectional action is more uniform.

The servo circuits 22 (FIG. 1) may be actuated to adjust proportions, compensate for wear, or for other reasons in response to the conductivity cell 20. To change the stroke ratios so as to maintain the proper concentration, the motor 52 is energized in the proper sense to cause the lead screw 53 to rotate the lead nut 140 up or down. Concurrently, therefore, the pin 37 is shifted relative to the pivot axis of the first linkage 36, causing a change in the length of the stroke of the concentrate metering piston 27, with a consequent change in the stroke ratios of the pistons 26, 27 and therefore a change in the output mixture, as previously described. Because of the angular displacement (approximately 24°) relative to the pivot point axis, there is even and properly proportioned delivery of water and concentrate throughout each cycle of movement.

The length of the adjustable range is limited, and this serves another useful purpose. Although the mixing ratio of water and concentrate can be varied for fine tuning purposes, there is an absolute limit determined by the physical constraints imposed by the slot 145 of FIG. 9 or the switches 170, 171 of FIG. 3. Even in the event of some unforeseen failure in the system, it is known that the mixing ratio will still be maintained within predetermined safe limits, as may be selected by a system designer. In addition, a convenient alarm feature is provided by the usage of the microswitches 170, 171 adjacent the opposite sides of the tab 141 extending from the lead nut 56. When the servo system seeks to shift the lead nut 56 outside the selected range, an error condition exists, perhaps as to the stability of the concentrate or a tendency to mechanical malfunction. Actuation of either limit switch 170, 171 therefore may be utilized to generate appropriate indication at an alarm display in the system.

Because of the smooth pumping action and constant proportionality between the water and concentrate parts of the system, only a relatively small chamber is required to mix these liquids. Sterilization of this part of the system by internal means is highly desirable, and this may be effected directly.

While a number of features and modifications have been described above, it should be appreciated that the invention is not limited thereto but encompasses all variations and forms within the scope of the appended claims.

What is claimed is:

1. A positive displacement system for delivery of two liquids at controlled rates using at least one pressurized liquid comprising:

first and second reciprocating piston means including first pivotally mounted linkage means coupled to reciprocate said piston means in synchronism, each for pumping a different liquid;

metering valve means including conduit means for controlling liquid flow directions through said piston means in response to the position of said metering valve means;

and control means including reciprocable actuator piston means, and switching valve means, and second pivotally mounted linkage means coupling said actuator piston means to reciprocate the metering valve means, said switching valve means being coupled to said first and second piston means and responsive to the position of said first and second piston means, said switching valve means being coupled to shift between limit positions synchronously with direction changes of said first and second piston means and controlling liquid flow to said actuator piston to shift said piston between limit positions synchronously with selected positions of said first and second piston means and reciprocate more rapidly than said first and second piston means.

2. The invention as set forth in claim 1 above, wherein said switching valve means includes connecting rod means adjacent said first linkage means, said connecting rod means including means engaging said first linkage mechanism adjacent each limit of pivoting movement thereof for shifting said switching valve means between opposite limit positions, wherein said metering valve means includes a pair of linear metering valves coupled to said second linkage means to shift in opposite directions, wherein a first of said metering valve means controls liquid inlet to said first and second piston means and the second of said metering valve means controls liquid outflow from said first and second piston means, and wherein each of said first and second piston means comprises a piston rod and connecting rod means coupled to said first linkage means, and said system further includes means engaging said second linkage means to limit the pivoting movement thereof in one direction such that metering flows through said first and second piston means in one direction are thereby diminished.

3. A proportioning pump system for providing controlled flows of water and concentrate for a dialysis machine, comprising:

reciprocable actuator means operative in response to water pressure and including a shiftable valve member, said actuator means shifting rapidly between limit positions under control of the position of the shiftable valve member;

water metering piston means reciprocable at a relatively slower rate than said actuator means in response to the direction of flow therethrough of pressurized water;

concentrate metering piston means;

first pivotally mounted linkage means coupling said water metering piston means and said concentrate metering piston means to reciprocate said piston means with a selected stroke length ratio between them; and coupled to shift said shiftable valve member in timed relation to reciprocation of said piston means;

second pivotally mounted linkage means coupled to said reciprocable actuator means;

metering valve means coupled to said second pivotally mounted linkage means and responsive to the position of said actuator means and coupled to control the direction of water and concentrate flow through the respective piston means; and means coupled to at least one of said piston means at the coupling to said first linkage means for varying the stroke length ratio between said piston means.

4. The system as set out in claim 3 above, wherein said means for varying the stroke length ratio comprises motor means mounted on said linkage means and follower means coupled to be driven by said motor means along a selected displacement axis, and wherein said one piston means includes connecting rod means coupled at one end to said follower means.

5. The system as set out in claim 4 above, wherein the displacement axis forms an angle of approximately 24° with an axis defined by the pivot point of said linkage means and the coupling points of said piston means thereto.

6. The system as set out in claim 3 above, wherein said system includes toggle linkage means coupling said first linkage means to said shiftable valve member, and arranged to shift said valve member between limit positions in synchronism with the limit positions of said linkage means.

7. The system as set out in claim 5 above, wherein said system further includes a pair of linear metering valves, each of the metering valves being coupled to be reciprocated by said second linkage means, a first of said metering valves controlling liquid ingress to said water and concentrate metering piston means and the second of said metering valves controlling liquid egress therefrom;

a body for containing said actuator means, said water and concentrate piston means, and said metering valves, said body including conduit means defining flow paths therebetween, wherein said first linkage means is mounted adjacent one side of said body and said second linkage means is mounted adjacent the opposite side of said body; and adjustable stop means positioned to limit the pivoting movement of said second linkage means in one direction, whereby to limit flow through said metering valves, and spring means engaging at least one of said piston means and said body, for mechanically compensating for play in the associated piston means.

8. A proportioning pumping system for a dialysate delivery system supplying water and concentrate in adjustable proportions within a predetermined range of proportions comprising:

a pivotable linkage mechanism;

a water metering piston movable along a first axis and coupled to a source of water and including connecting rod means coupled to a first region of said linkage mechanism;

a concentrate metering piston movable along a line parallel to the first axis and coupled to a source of concentrate and including connecting rod means coupled to said first linkage mechanism at a second region thereof;

means coupled to said linkage mechanism and at least one of said connecting rod means for adjusting the piston stroke ratio of the two pistons;

means coupled to the water and concentrate metering pistons for mixing metered flows from the two pistons;

means coupled to receive the mixed flows for indicating the concentrate proportion in the mixture; and means coupled to the means for indicating and responsive to the indication of concentrate proportion and coupled to said means for adjusting for altering the stroke ratios to tend to maintain a constant concentrate proportion.

9. The invention as set forth in claim 8 above, wherein said means for adjusting comprises means defining a displacement path along said linkage mechanism and follower means coupled to one of said connecting rod means, the displacement path lying along an axis having a substantial included angle relative to the axis defined by the pivot, first region and second region of said linkage mechanism.

10. The invention as set forth in claim 9 above, wherein said means for adjusting further comprises drive motor means mounted on said linkage mechanism, and lead screw means coupled to be driven by said drive motor means and controlling of the position said follower means.

11. The invention as set forth in claim 10 above, including switch means mounted on said linkage mechanism and positioned to be actuated at individual limit positions of said follower means.

12. The invention as set forth in claim 11 above, including in addition metering valve means disposed in the flow paths to said water metering piston and concentrate metering piston and responsive to the position of said linkage mechanism for controlling liquid flow through said pistons;

bistable hydraulic means responsive to the position of said linkage mechanism and coupled to control the position of said metering valve means such as to maintain the metering valve means in each of two different positions for the greater part of the stroke of said pistons, wherein said bistable hydraulic means comprises switching valve means disposed along an axis parallel to the first axis and actuator piston means coupled to said metering valve means, said switching valve means being coupled to said metering valve means and coupled to control the flow of pressurized water to said actuator piston means; and wherein said switching valve means is coupled to said linkage mechanism by a connecting rod member having limit stops engaging a portion of said linkage mechanism and substantial freedom of movement between said limit stops.

13. The invention as set forth in claim 12 above, wherein said metering valve means comprise slide valve means disposed along axes substantially parallel to the axis of said switching piston means, and including in addition a second pivotable linkage mechanism coupled to said actuator piston.

* * * * *

UNITED STATES PATENT AND TRADEMARK OFFICE
CERTIFICATE OF CORRECTION

PATENT NO. : 4,360,323
DATED : November 23, 1982
INVENTOR(S) : Robert L. Anderson It is certified that error appears in the above-identified patent and that said Letters Patent are hereby corrected as shown below:

Column 5, line 24, after "at" and before "concentrate", "thee" should read --the--;

Column 7, line 29, should read $$-f_1(a_1 + \delta a_1, \delta\theta_1)--$$

Column 14, line 32, after "controlling", strike "of"; line 32, after "position", insert --of--.

Signed and Sealed this

Seventeenth Day of May 1983

[SEAL]

Attest:

DONALD J. QUIGG

Attesting Officer    Acting Commissioner of Patents and Trademarks